United States Patent

Sawamura et al.

[11] Patent Number: 5,993,535
[45] Date of Patent: Nov. 30, 1999

[54] CALCIUM PHOSPHATE CEMENT AND CALCIUM PHOSPHATE CEMENT COMPOSITION

[75] Inventors: Takenori Sawamura; Masateru Hattori; Masahiko Okuyama, all of Nagoya, Japan

[73] Assignee: NGK Spark Plug Co., Ltd., Aichi, Japan

[21] Appl. No.: 09/141,516

[22] Filed: Aug. 27, 1998

[30] Foreign Application Priority Data

Aug. 28, 1997 [JP] Japan ................................. 9-250083
Aug. 28, 1997 [JP] Japan ................................. 9-250084

[51] Int. Cl.$^6$ .......................... C04B 12/02; C04B 24/38
[52] U.S. Cl. .......................... 106/691; 106/35; 106/690; 433/228.1; 606/76; 623/16
[58] Field of Search ........................ 106/35, 690, 691; 433/228.1; 606/76; 623/16

[56] References Cited

U.S. PATENT DOCUMENTS

| Re. 33,161 | 2/1990 | Brown et al. ............................ 423/308 |
| 5,152,836 | 10/1992 | Hirano et al. ........................... 106/690 |
| 5,180,426 | 1/1993 | Sumita ..................................... 106/35 |
| 5,281,404 | 1/1994 | Sumita ..................................... 423/305 |
| 5,342,441 | 8/1994 | Mandai et al. ............................ 106/35 |

FOREIGN PATENT DOCUMENTS

| 0 436 499 | 7/1991 | European Pat. Off. ......... C01B 25/32 |
| 0 298 501 | 4/1992 | European Pat. Off. ......... A61K 6/06 |
| 0 323 632 | 7/1992 | European Pat. Off. ......... A61K 6/06 |
| 59-88351 | 5/1984 | Japan ............................. C04B 13/00 |
| 59-222408 | 12/1984 | Japan . |
| 62-83348 | 4/1987 | Japan ............................. C04B 28/34 |
| 1-100048 | 4/1989 | Japan ............................. C04B 28/34 |
| 2-77261 | 3/1990 | Japan ............................. A61L 25/00 |
| 2-102165 | 4/1990 | Japan ............................. C04B 35/00 |
| 3-112843 | 5/1991 | Japan ............................. C04B 28/34 |
| 3-141955 | 6/1991 | Japan ............................. A61L 27/00 |
| 6-199622 | 7/1994 | Japan . |
| 7-289627 | 11/1995 | Japan ............................. A61L 27/00 |
| 2 074 702 | 3/1997 | Russian Federation . |
| 2 248 232 | 4/1992 | United Kingdom . |
| 96/02259 | 2/1996 | WIPO ........................... A61K 31/725 |

OTHER PUBLICATIONS

JAPIO Patent Abstract No. JP402297374A, abstract of Japanese Patent Specification No. 02–297374, (Dec. 1990).
JAPIO Patent Abstract No. JP403128061A, abstract of Japanese Patent Specification No. 03–128061, (May 1991).
JAPIO Patent Abstract No. JP407039577A, abstract of Japanese Patent Specification No. 07–039577, (Feb. 19995).

*Primary Examiner*—Anthony Green
*Attorney, Agent, or Firm*—Sughrue, Mion, Zinn, Macpeak & Seas, PLLC

[57] ABSTRACT

A calcium phosphate cement and a calcium phosphate cement composition are disclosed. The calcium phosphate cement comprises a calcium phosphate powder having an average particle diameter of 20 μm or smaller and a tap density of 35% or higher, and a polysaccharide. The polysaccharide is preferably a dextran sulfate (e.g., dextran sulfate sodium) having an average particle diameter of 0.1 to 100 μm. The calcium phosphate cement composition comprises the above specific calcium phosphate powder and a liquid for cement mixing comprising an aqueous solution containing 30 to 60 wt % dextran sulfate (e.g., dextran sulfate sodium or dextran sulfate potassium). The calcium phosphate powder preferably comprises a tetracalcium phosphate powder and an equimolar amount of a calcium hydrogen phosphate powder as main components.

9 Claims, No Drawings

CALCIUM PHOSPHATE CEMENT AND CALCIUM PHOSPHATE CEMENT COMPOSITION

BACKGROUND OF THE INVENTION

1. Field of the Invention

The present invention relates to a calcium phosphate cement which comprises a calcium phosphate powder and a polysaccharide incorporated therein and which, due to this composition, can be hardened easily in a relatively short time using only water not containing an organic acid or the like. The present invention further relates to a calcium phosphate cement composition which comprises a calcium phosphate powder, a polysaccharide, and water, and which can be easily hardened in a relatively short time, especially when an aqueous solution containing the polysaccharide has been used as a liquid for cement mixing.

2. Description of the Related Art

A large number of medical cements of various compositions have previously been proposed for use in living bodies. Calcium phosphate cements for living bodies have an advantage in that this kind of cement upon hardening changes into a bioactive hydroxyapatite, and hence results in a hardened cement having excellent bioaffinity.

Many of the calcium phosphate cements for living bodies comprise tetracalcium phosphate as the main component; see, for example, U.S. Pat. No. 4,612,053, now Reissue Pat. No. 33,161. However, this kind of-cement has a problem in practical use because it requires a relatively long time for hardening. There is also a problem that when a cement paste prepared therefrom is brought into contact with a pseudo body fluid immediately after mixing (i.e., kneading), water penetrates into the paste (i.e., kneaded body) and disintegrates the paste. Consequently, two different methods have been used to apply the cement to a body part where body fluids are present in a large amount. The first method is to apply a cement paste, not immediately after mixing, but instead after it has hardened to some degree. The second method is to apply the cement paste after removal of the body fluids from the body part and after hemostasis, etc. However, these two methods suffer drawbacks in that the cement paste which has hardened to some degree is difficult to handle and has poor workability, and the removal of body fluids, hemostasis, and the like require many hands and much time.

As an expedient for eliminating these problems, a technique for reducing the hardening time using an aqueous solution of either an organic acid (e.g., citric acid or malic acid) or an inorganic acid (e.g., phosphoric acid) as a liquid for cement mixing (i.e., kneading liquid) has been proposed in, for example, JP-A-59-88351 and JP-A-62-83348; the term "JP-A" as used herein means an "unexamined published Japanese patent application". However, when a cement paste prepared with a cement-mixing liquid containing an acid is applied to an inner part of a living body, the paste is highly biostimulative due to the acid, and may cause an inflammatory reaction around the body part to which the paste has been applied. JP-A-2-77261 describes a technique of using an aqueous solution containing chitosan, etc. as a hardener solution so as to inhibit cement disintegration. However, this hardener solution should have a very low pH of approximately 1 to 2, so as to contain the chitosan dissolved therein, and therefore the addition of an acid to the hardener solution is unavoidable. Consequently, this technique also may have the problem of causing an inflammatory reaction, etc. as in the above-described technique.

SUMMARY OF THE INVENTION

The present invention eliminates the problems described above by providing a calcium phosphate cement and a calcium phosphate cement composition which both require a relatively short hardening time and are free from cement paste disintegration even when applied and brought into contact with body fluids immediately after mixing. Since the calcium phosphate cement and the calcium phosphate cement composition do not necessitate a cement-mixing liquid containing an acid and having a lowered pH, they have reduced biostimulation and do not pose problems such as inflammatory reactions.

DETAILED DESCRIPTION OF THE PREFERRED EMBODIMENTS

The calcium phosphate cement according to a first embodiment of the present invention comprises a calcium phosphate powder having an average particle diameter of 20 $\mu$m or smaller and a tap density of 35% or higher, and a polysaccharide.

The calcium phosphate cement composition according to a second embodiment of the present invention comprises a calcium phosphate powder having an average particle diameter of 20 $\mu$m or smaller and a tap density of 35% or higher, a polysaccharide, and water.

The calcium phosphate cement composition according to a third embodiment of the present invention comprises a calcium phosphate powder having an average particle diameter of 20 $\mu$m or smaller and a tap density of 35% or higher and a liquid for cement mixing which comprises an aqueous solution containing a polysaccharide.

The above-described compositions of the second and third embodiments are each an unhardened composition comprising a calcium phosphate powder, a polysaccharide, and water. In practical use, these compositions are prepared according to a method comprising the steps of preparing a saccharide-containing liquid for cement mixing, and then mixing this liquid with the powder, such as the powder of the third embodiment.

The aforementioned average particle diameter for a calcium phosphate powder can be determined by a laser diffraction type particle size distribution analyzer (e.g., Type "LA-500", manufactured by Horiba Ltd.) using a dispersion medium in which calcium phosphate particles do not dissolve; examples of the dispersion medium include but are not limited to water, methanol and ethanol. The aforementioned tap density for a calcium phosphate powder can be calculated using the following equation (1):

$$\text{Tap density} = [W/(D \times V_{tap})] \times 100 \ (\%)$$

where $V_{tap}$ is the volume of the calcium phosphate powder measured after packing the powder into a given vessel and repeatedly oscillating the vessel until the powder volume becomes constant; W is the weight of the powder; and D is the true specific gravity of the calcium phosphate constituting the powder.

By regulating the average particle diameter of the calcium phosphate powder to 20 $\mu$m or smaller, as in the first embodiment, the powder particles show enhanced adhesion to one another and the reactions for hardening are accelerated. Furthermore, by regulating the tap density of the powder to 35% or higher, the powder particles are in closer contact with one another during mixing, and the time required for hardening is further reduced. If a calcium phosphate powder having an average particle diameter exceeding 20 μm is used, the powder less readily dissolves in a liquid for cement mixing, resulting in a longer hardening time. If a calcium phosphate powder having a tap density lower than 35% is used, the powder particles are in less sufficient contact with one another during mixing and the reactions for hardening are not accelerated as much, resulting in a longer hardening time.

By regulating the average particle diameter of the calcium phosphate powder to 15 μm or smaller as in one aspect of the first embodiment, particularly to 1 to 10 μm, the powder has enhanced solubility in a liquid for cement mixing, resulting in a reduced hardening time. Furthermore, by regulating the tap density of the powder to 40% or higher, particularly to 45 to 60%, the powder particles more readily come into contact with one another during mixing and the reactions for hardening are accelerated, resulting in a further reduced hardening time. In the calcium phosphate cement compositions of the second and third embodiments, it is preferable to regulate the average particle diameter and tap density of the calcium phosphate powder to values within the respective ranges shown above, because the same effects are produced thereby. The lower limit of the average particle diameter of the calcium phosphate powder is generally 1 μm, while the upper limit of tap density thereof is generally 60%.

Usable examples of the calcium phosphate powder include powders of tetracalcium phosphate, calcium hydrogen phosphate, tricalcium α-phosphate, tricalcium β-phosphate, and the like. These powders may be used alone or in combinations of two or more. An X-ray contrast medium (e.g., barium sulfate or bismuth subcarbonate) may be incorporated into this powder. It is also possible to add a hydroxyapatite, a fluoride, or the like as seed crystals in order to reduce the hardening time.

A preferable calcium phosphate powder comprises powders of tetracalcium phosphate and calcium hydrogen phosphate as the main components of another aspect of the first embodiment. Although the proportions of these two powders are not particularly limited, the two powders are preferably used in a molar ratio of 8/2 to 2/8, more preferably 6/4 to 4/6, and most preferably about 1/1. In the calcium phosphate cement compositions of the second and third embodiments also, it is preferable to use a calcium phosphate powder comprising powders of tetracalcium phosphate and calcium hydrogen phosphate as the main components preferably in a molar ratio in the above range.

The term "main components" used above means that the total amount of the two powders based on the whole amount of the calcium phosphate powder is at least 60% by weight, and preferably at least 80% by weight. By using those two powders in combination as the main components, the cement paste is less susceptible to disintegration and is capable of easily retaining a given shape.

Processes for producing the tetracalcium phosphate powder are not particularly limited, and a powder produced by any process can be used. For example, use may be made of a powder produced by preparing an equimolar mixture of calcium carbonate and calcium hydrogen phosphate, molding the mixture into a given shape, sintering the shape at a temperature in the range of 1,450 to 1,550° C., and then pulverizing the sintered shape into a powder having an average particle diameter of about 100 μm. As the calcium hydrogen phosphate powder, a commercial product of either calcium hydrogen phosphate dihydrate or anhydrous calcium hydrogen phosphate can be used in its commercial form. It is also possible to use a powder obtained by dehydrating the commercial dihydrate by heating it at about 120° C. However, the calcium hydrogen phosphate powder for use in the present invention should not be construed as being limited to these powders.

As the polysaccharide, a polysaccharide formed from any of various monosaccharides through polyglycosylation can be used. An especially preferable polysaccharide is a dextran sulfate as in other aspects of the first to third embodiments. More preferable examples of this dextran sulfate include dextran sulfate sodium and dextran sulfate potassium.

In the calcium phosphate cement of the first embodiment, it is preferable to use a dextran sulfate having an average particle diameter of 0.1 to 100 μm, more preferably 1 to 80 μm, and most preferably 10 to 60 μm. If a dextran sulfate having an average particle diameter smaller than 0.1 μm is used, the cement results in a paste having a low viscosity and, hence, impartation of a given shape thereto is less likely. On the other hand, if a dextran sulfate having an average particle diameter exceeding 100 μm is used, it is not as evenly dispersed and incorporated into a calcium phosphate powder and the resultant cement gives a paste less inhibited from disintegrating upon contact with body fluids. The average particle diameter of a dextran sulfate can be determined using the same apparatus and the same operation as in the case of the calcium phosphate powder.

The content of the dextran sulfate is preferably 5 to 25 parts by weight as another aspect of the first embodiment, and more preferably 10 to 20 parts by weight per 100 parts by weight of the calcium phosphate powder. If the content of the dextran sulfate is below 5 parts by weight, the cement results in a paste having a low viscosity and, hence, shape impartation thereto is difficult. In addition, when such a paste comes into contact with body fluids, it disintegrates somewhat and is less likely to retain the given shape. On the other hand, if the content of the dextran sulfate exceeds 25 parts by weight, the excess dextran sulfate inhibits the reactions for hardening, resulting in a prolonged hardening time. In some cases, hardened cement cannot be obtained therefrom.

Dextran sulfates readily dissolve in water. When a dextran sulfate is incorporated into a calcium phosphate cement, the hardening time of the cement can be reduced without adding an acid to the water, preferably pure water, used as a cement-mixing liquid. Furthermore, even when the paste is brought into contact with body fluids immediately after mixing, it never disintegrates. Moreover, since there is no need to use an acid for mixing, the cement can be mixed and hardened at a relatively high pH. Namely, the pH of the cement paste during mixing and hardening is not so low as to cause inflammatory reactions. Consequently, not only the periphery of the part to which the paste has been applied does not suffer an inflammatory reaction or the like during hardening, but also the resultant hardened cement does not adversely influence the body tissues. In addition, since the cement paste has a moderate viscosity and excellent handleability, it can be easily made to have a given shape.

The calcium phosphate cement composition of the third embodiment preferably contains a dextran sulfate in an amount of 30 to 60 parts by weight, more preferably 35 to 55 parts by weight, most preferably 40 to 50 parts by weight, per 100 parts by weight of the liquid for cement mixing. If the content of the dextran sulfate is below 30 parts by weight, the cement paste, when brought into contact with body fluids immediately after mixing, tends to disintegrate and is less likely to retain a given shape. On the other hand, if the content thereof exceeds 60 parts by weight, the cement paste has a high viscosity and, hence, shape impartation thereto is not easy. In the second embodiment also, the proportion of the polysaccharide to the water is preferably in the same range as described above, whereby the same effects can be obtained.

The composition containing an appropriate amount of a polysaccharide (e.g., a dextran sulfate) and the composition prepared with a cement-mixing liquid consisting of an aqueous solution containing the polysaccharide have excellent suitability for mixing and can be easily handled. Since the aqueous solution containing a dextran sulfate or the like dissolved therein has a considerably high viscosity and functions to bond calcium phosphate particles to one another, the cement paste obtained is excellent in the ability to be shaped. Moreover, since a dextran sulfate readily dissolves in water to give a homogeneous aqueous solution which has a pH of 5 to 8 and is hence neutral, the cement paste is less biostimulative and does not cause an inflammatory reaction. Furthermore, since the aqueous solution serves to maintain the contact or bonding among calcium phosphate particles until the cement composition hardens, the cement paste is less apt to disintegrate even in contact with body fluids and can reside in the body part to which the paste has been applied, while retaining a given shape. In addition, since the polysaccharide and water used in the cement composition are gradually released from the cement paste during hardening, the reactions for hardening are not inhibited.

In the calcium phosphate cement of the first embodiment and in the calcium phosphate cement compositions of the second and third embodiments, the calcium phosphate particles change into a hydroxyapatite through hardening. The hardened cement thus formed has a strength sufficient for use as a bone supplement filling material, etc., and is excellent in bioaffinity, bioactivity, etc. Therefore, the cement and the cement compositions are especially useful in applications in which an artificial bone, artificial joint, artificial tooth root, or the like combining excellent strength and excellent bioactivity is formed. The term impartation of a shape used above means both the initial impartation of a shape and the shape correction or modification conducted after application, etc.

The viscosity of a cement paste may be regulated by changing the proportion of the calcium phosphate cement of the first embodiment or the calcium phosphate powder in the second or third embodiment to the water used as a cement-mixing liquid or as the main component of the liquid. The proportion of the cement or powder to the water is preferably regulated to such a value that the amount of the water is about 10 to 40 parts by weight per 100 parts by weight of the calcium phosphate cement or calcium phosphate powder. The proportion of water is more preferably 15 to 35 parts by weight, and most preferably 20 to 30 parts by weight.

If the proportion of water is too small, the cement paste has a high viscosity and, hence, impartation of a given shape thereto is more difficult. On the other hand, large proportions of water are undesirable in that the resultant cement paste has a reduced viscosity and is apt to disintegrate upon contact with body fluids, although satisfactory in handleability. When a cement paste having a moderately reduced viscosity is prepared by increasing the proportion of water, this paste can be applied with a syringe to a body part suffering from bone deficiency, fracture, etc., whereby the burden to the patient can be alleviated.

The cement paste prepared from the calcium phosphate cement of the first embodiment and those prepared from the calcium phosphate cement compositions of the second and third embodiments each can be applied alone in vivo in applications such as an artificial bone, artificial tooth root, etc. Furthermore, it is also possible to add a bone-forming factor, antitumor agent, antibiotic, etc. during cement/water mixing to use the resulting hardened cement as a carrier for gradual drug release.

Examples of the present invention will be given below.

Examples Corresponding to Calcium Phosphate Cement of the First Embodiment

EXAMPLE 1

To 100 g of an equimolar mixture (average particle diameter, 5.5 $\mu$m; tap density, 52%) of a tetracalcium phosphate powder and a powder of anhydrous calcium hydrogen phosphate was added 10 g of Dextran sulfate sodium sulfur 5 (average particle diameter, 50 $\mu$m; average molecular weight, 2,000; manufactured by Meito Sangyo K. K.). The two ingredients were mixed with each other by means of a resin pot for 1 hour to prepare a calcium phosphate cement. This cement is referred to as cement A.

EXAMPLE 2

To 100 g of an equimolar mixture (average particle diameter, 3.2 $\mu$m; tap density, 46%) of a tetracalcium phosphate powder and a powder of anhydrous calcium hydrogen phosphate was added 20 g of Dextran sulfate sodium sulfur 5 (average particle diameter, 20 $\mu$m; average molecular weight, 2,000; manufactured by Meito Sangyo K. K.). The two ingredients were mixed with each other by means of a resin pot for 1 hour to prepare a calcium phosphate cement. This cement is referred to as cement B.

COMPARATIVE EXAMPLE 1

To 100 g of an equimolar mixture (average particle diameter, 2.2 $\mu$m; tap density, 34%) of a tetracalcium phosphate powder and a powder of anhydrous calcium hydrogen phosphate was added 10 g of Dextran sulfate sodium sulfur 5 (average particle diameter, 50 $\mu$m; average molecular weight, 2,000; manufactured by Meito Sangyo K. K.). The two ingredients were mixed with each other by means of a resin pot for 1 hour to prepare a calcium phosphate cement. This cement is referred to as cement C.

COMPARATIVE EXAMPLE 2

To 100 g of an equimolar mixture (average particle diameter, 22 $\mu$m; tap density, 55%) of a tetracalcium phosphate powder and a powder of anhydrous calcium hydrogen phosphate was added 10 g of Dextran sulfate sodium sulfur 5 (average particle diameter, 50 $\mu$m; average molecular weight, 2,000; manufactured by Meito Sangyo K. K.). The two ingredients were mixed with each other by means of a resin pot for 1 hour to prepare a calcium phosphate cement. This cement is referred to as cement D.

EXPERIMENTAL EXAMPLE 1

One gram of each of cements A to D was mixed with 0.25 g of pure water, and each resultant paste was examined for hardening time in accordance with JIS T 6602. As a result, the hardening times of cements A and B were found to be 12 minutes and 15 minutes, respectively, and those of cements C and D were found to be 39 minutes and 50 minutes, respectively. The results show the following. The calcium phosphate cements according to the present invention rapidly hardened upon mixing only with water not containing an organic acid or the like. In contrast, cement C, in which the tap density of the calcium phosphate powder was below the lower limit specified in the first embodiment, had a hardening time two to three times those of cements A and B. Further, cement D, in which the average particle diameter of the calcium phosphate powder was above the upper limit specified in the first embodiment, required an even longer hardening time than cement C.

EXPERIMENTAL EXAMPLE 2

One gram of cement A was mixed with 0.23 g of pure water for 2 minutes. The resultant paste had moderate viscosity and shape impartation thereto was easy. This paste was molded by packing it into a mold having a cavity with an inner diameter of 6 mm and a depth of 5 mm, and the molded paste was taken out of the mold and immersed in a pseudo body fluid. As a result, the molded paste retained its shape without disintegrating. Furthermore, the molded paste was immersed in a 37° C. pseudo body fluid for 24 hours to obtain a hardened cement. The structural crystalline phase of this hardened cement was analyzed by X-ray diffraction. As a result, the crystalline phase was ascertained to be made of a hydroxyapatite and tetracalcium phosphate.

EXPERIMENTAL EXAMPLE 3

One gram of cement A was mixed with 0.3 g of pure water for 5 minutes. The resultant paste had a low viscosity and could be extruded with an 18-gage syringe. This extrudate was immersed in a 37° C. pseudo body fluid for 24 hours to obtain a hardened cement. The structural crystalline phase of this hardened cement was analyzed by X-ray diffraction. As a result, the crystalline phase was ascertained to be made of a hydroxyapatite and tetracalcium phosphate.

Examples Corresponding to Calcium Phosphate Cement Composition of the Second Embodiment
(1) Production of Calcium Phosphate Powder

PRODUCTION EXAMPLE 1

A tetracalcium phosphate powder having an average particle diameter of 90 μm was mixed with an equimolar amount of a powder of anhydrous calcium hydrogen phosphate having an average particle diameter of 20 μm by means of an automatic mortar for 30 minutes to obtain a calcium phosphate powder having an average particle diameter of 5.5 μm and a tap density of 52%. This powder is referred to as powder A.

PRODUCTION EXAMPLE 2

A tetracalcium phosphate powder having an average particle diameter of 30 μm was mixed with an equimolar amount of a powder of anhydrous calcium hydrogen phosphate having an average particle diameter of 20 μm by means of an automatic mortar for 30 minutes to obtain a calcium phosphate powder having an average particle diameter of 3.2 μm and a tap density of 46%. This powder is referred to as powder B.

PRODUCTION EXAMPLE 3

A tetracalcium phosphate powder having an average particle diameter of 5 μm was mixed with an equimolar amount of a powder of anhydrous calcium hydrogen phosphate having an average particle diameter of 20 μm by means of an automatic mortar for 30 minutes to obtain a calcium phosphate powder having an average particle diameter of 2.2 μm and a tap density of 32%. This powder is referred to as powder C.

PRODUCTION EXAMPLE 4

A tetracalcium phosphate powder having an average particle diameter of 90 μm was mixed with an equimolar amount of a powder of anhydrous calcium hydrogen phosphate having an average particle diameter of 20 μm by means of an automatic mortar for 10 minutes to obtain a calcium phosphate powder having an average particle diameter of 22 μm and a tap density of 60%. This powder is referred to as powder D.

In Examples 1 and 2, Comparative Examples 1 and 2, Experimental Examples 4 and 5, and Production Examples 1 to 4, the tap density of each calcium phosphate powder was determined by placing 10 g of the powder in a measuring cylinder having a capacity of 25 ml, tapping the cylinder from a height of about 3 cm 100 times, measuring the resultant volume of the powder to obtain a value of $V_{tap}$, and calculating the tap density using equation (1) given hereinabove.

EXPERIMENTAL EXAMPLE 4

One gram of each of calcium phosphate powders A to D was mixed with 0.25 g of a cement-mixing liquid consisting of a 50 wt % aqueous solution of Dextran sulfate sodium sulfur 5 (average molecular weight, 2,000; manufactured by Meito Sangyo K. K.). Each resultant paste was examined for hardening time in accordance with JIS T 6602. As a result, the hardening times of powders A and B were found to be 8 minutes and 12 minutes, respectively, and those of powders C and D were found to be 36 minutes and 42 minutes, respectively.

The above results show the following. The calcium phosphate cement compositions according to the second embodiment hardened rapidly due to the function of the dextran sulfate incorporated therein, even though the cement-mixing liquid therefor did not contain an organic acid or the like. In contrast, powder C, which was a calcium phosphate powder having a tap density below the lower limit specified in the second embodiment, had a hardening time at least three to four times those of powders A and B. Further, powder D, which was a calcium phosphate powder having an average particle diameter above the upper limit specified in the second embodiment, required an even longer hardening time than powder C.

EXPERIMENTAL EXAMPLE 5

One gram of powder A was mixed with 0.23 g of the above cement-mixing liquid for 2 minutes. The paste obtained had a moderate putty-like consistency and shape impartation thereto was easy. This paste was molded by packing it into a mold having a cavity with an inner diameter of 6 mm and a depth of 5 mm, and the molded paste was taken out of the mold and immersed in a pseudo body fluid. As a result, the molded paste retained its shape without disintegrating. Furthermore, the molded paste was immersed in a 37° C. pseudo body fluid for 24 hours to obtain a hardened cement. The structural crystalline phase of this hardened cement was analyzed by X-ray diffraction. As a result, the crystalline phase was ascertained to be made of a hydroxyapatite and tetracalcium phosphate.

EXPERIMENTAL EXAMPLE 6

One gram of powder A was mixed with 0.3 g of a cement-mixing liquid consisting of a 40 wt % aqueous solution of Dextran sulfate sodium sulfur 5 (average molecular weight, 5 2,000; manufactured by Meito Sangyo K. K.) for 5 minutes. The resultant paste had a low viscosity and could be extruded with an 18-gage syringe. This extrudate was immersed in a 37° C. pseudo body fluid for 24 hours to obtain a hardened cement. The structural crystalline phase of this hardened cement was analyzed by X-ray diffraction. As a result, the crystalline phase was ascertained to be made of a hydroxyapatite and tetracalcium phosphate.

The calcium phosphate cement of the first embodiment can be hardened using water alone in a relatively short time, and the paste obtained therefrom retains its shape without disintegrating even when brought into contact with a pseudo body fluid immediately after mixing. The cement has moderate viscosity during mixing and has excellent shaping ability. Furthermore, since the cement does not necessitate the addition of an organic acid or the like thereto for hardening acceleration, it does not produce adverse influences on the patient, such as inflammatory reactions during mixing and during the reactions for hardening.

The calcium phosphate cement compositions of the second and third embodiments can be hardened in a relatively short time, and the pastes thereof retain their shape without disintegrating even when brought into contact with a pseudo body fluid immediately after mixing. The cement compositions have moderate viscosity during-mixing and have excellent shaping ability. Furthermore, since the cement compositions do not necessitate the addition of an organic acid or the like thereto for hardening acceleration, they do not produce adverse influences on the patient, such as inflammatory reactions during mixing and during the reactions for hardening.

The entire disclosure of each and every foreign patent application from which the benefit of foreign priority has been claimed in the present application is incorporated herein by reference, as if fully set forth.

While only certain embodiments of the invention have been specifically described herein, it will apparent that numerous modifications may be made thereto without departing from the spirit and scope of the invention.

What is claimed is:

1. A calcium phosphate cement comprising a calcium phosphate powder having an average particle diameter of 20 $\mu$m or smaller and a tap density of 35% or higher, and dextran sulfate.

2. The calcium phosphate cement of claim 1, wherein the calcium phosphate powder has an average particle diameter of 15 $\mu$m or smaller and a tap density of 40% or higher.

3. The calcium phosphate cement of claim 1, wherein the calcium phosphate powder comprises tetracalcium phosphate and calcium hydrogen phosphate, wherein the total amount of tetracalcium phosphate and calcium hydrogen phosphate is at least 60% by weight of the whole amount of calcium phosphate powder.

4. The calcium phosphate cement of claim 1, wherein the dextran sulfate has an average particle diameter of 0.1 to 100 $\mu$m.

5. The calcium phosphate cement of claim 1, wherein the amount of the dextran sulfate is 5 to 25 parts by weight per 100 parts by weight of the calcium phosphate powder.

6. A calcium phosphate cement composition comprising a calcium phosphate powder having an average particle diameter of 20 $\mu$m or smaller and a tap density of 35% or higher, a dextran sulfate, and water.

7. The calcium phosphate cement composition of claim 6 wherein the dextran sulfate, the amount of the dextran sulfate is 30 to 60 parts by weight per 100 parts by weight of the water for cement mixing.

8. A calcium phosphate cement composition comprising a calcium phosphate powder having an average particle diameter of 20 $\mu$m or smaller and a tap density of 35% or higher, and an aqueous solution containing water for cement mixing and dextran sulfate.

9. The calcium phosphate cement composition of claim 8 wherein the amount of the dextran sulfate is 30 to 60 parts by weight per 100 parts by weight of the liquid for cement mixing.

* * * * *

UNITED STATES PATENT AND TRADEMARK OFFICE
CERTIFICATE OF CORRECTION

PATENT NO. : 5,993,535
DATED : November 30, 1999
INVENTOR(S) : Takenori SAWAMURA et al It is certified that error appears in the above-identified patent and that said Letters Patent is hereby corrected as shown below:

In claim 7, at column 10, line 26, after "wherein" delete "the dextran sulfate,".

Signed and Sealed this

Eighth Day of August, 2000

Attest:

Q. TODD DICKINSON

Attesting Officer

Director of Patents and Trademarks